United States Patent [19]

de Weck et al.

[11] 4,415,492

[45] Nov. 15, 1983

[54] LYSINE POLYMERS WHICH MAY BE USED AS SUPPORTS FOR THE PREPARATION OF PRODUCTS OF DIAGNOSIS AND PRODUCTS OBTAINED

[75] Inventors: Alain L. de Weck, Institut für klinische Immunologie, Bern, Switzerland, 3010; Conrad H. Schneider; Hans P. Rolli, both of Bern, Switzerland

[73] Assignees: Alain L. de Weck; Institut fur Immunologie Inselspital, both of Bern, Switzerland

[21] Appl. No.: 292,358

[22] Filed: Aug. 13, 1981

[30] Foreign Application Priority Data

Aug. 29, 1980 [FR] France .................................. 80 18809

[51] Int. Cl.$^3$ ........................................... C07C 103/52
[52] U.S. Cl. ............................................... 260/112.5 R
[58] Field of Search ......................................... 424/177

[56] References Cited

U.S. PATENT DOCUMENTS 2,932,635 4/1960 Amiard et al. ............... 260/112.5 R
3,215,684 11/1965 Strojny et al. ............... 260/112.5 R
3,907,755 9/1975 Margraff et al. ..................... 424/78

OTHER PUBLICATIONS

Chemical Abstracts, 70, 384(1969), Abstract No. 43834k.
Chemical Abstracts, 96, 9(1982), Abstract No. 69557m.
Chemical Abstracts, 96, 325(1982), Abstract No. 186251z.

*Primary Examiner*—Delbert R. Phillips
*Assistant Examiner*—F. T. Moezie
*Attorney, Agent, or Firm*—Poms, Smith, Lande & Rose

[57] ABSTRACT

The present invention relates to lysine polymers of one of the following formulae:

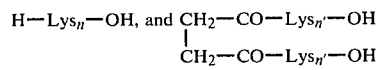

in which n is a whole number from 8 to 20 and n' a whole number from 4 to 10, to their process of preparation and to their use for the preparation of products of conjugation with benzylpenicillin or any other antibiotic of the β-lactam type, which serve as products of diagnosis for skin tests intended to reveal an allergy to penicillin or any other antibiotic of the β-lactam type.

2 Claims, No Drawings

LYSINE POLYMERS WHICH MAY BE USED AS SUPPORTS FOR THE PREPARATION OF PRODUCTS OF DIAGNOSIS AND PRODUCTS OBTAINED

The present invention relates to new lysine polymers which may be used as supports for the preparation of products of diagnosis and, in particular, for the preparation of penicilloyl-polylysines for the diagnosis of allergies to penicillins and other $\beta$-lactam type antibiotics. It also relates to a process for preparing such lysine polymers and to the products of diagnosis obtained by using said polymers.

In 1960, products of degradation of penicillin, and in particular benzylpenicillanic acid, were identified as being responsible for the formation of antigenic determinants involved in allergy to penicillin. The main antigenic determinant responsible was then identified as being the benzylpenicilloyl (BPO) group. In 1962, Parker and de Weck prepared, for the first time, a conjugate of the benzylpenicilloyl groups with a polymer of L-lysine. This reagent was then soon used as cutaneous test for revealing the hypersensitivity of patients allergic to penicillin. Since then, numerous studies on this type of reagent, usually known by the abbreviation PPL, have been published both in the United States and in Europe.

Although the use of PPL as cutaneous reagent for revealing allergy to penicillin is generally acknowledged, several factors have hitherto prevented its production on an industrial scale. These factors are as follows:

Firstly, the L-lysine polymers heretofore used as vehicles of the BPO groups are prepared by a random polymerisation according to a known process (Katchalski et col., Prot. Chem. 13, 243, 1958). This results in a considerable heterogeneity in the distribution of the molecular weights of the L-lysine polymers thus obtained and probably also in the degree of substitution of the individual molecules by the BPO groups. Even under controlled conditions, the distribution of the molecular weights of the preparations of PPL is difficult to reproduce from one batch to the other. The heterogeneity of the preparations of PPL currently used up to the present time is probably the main cause of the divergences observed in the results obtained with various preparations. It has therefore appeared desirable, for the preparation of these products of diagnosis, to have a reproducible and perfectly well defined polylysine support, thus giving consistent results on the biological plane. This is one of the objects of the present invention.

On the other hand, it was shown a few years ago that, for the BPO-poly-lysines to provoke on the skin of the patients or animals hypersensitive to penicillins, the desired reactions of erythema and of papules, the small bivalent molecules of BPO are not very effective, whilst an optimal reactivity appears to be due to the presence of molecules of BPO of average size, containing from 3 to 6 BPO groups per molecule. (Levine B. B., Fellner M. J. J. Allergy, 36, 342, 1965). Recent studies with homogeneous BPO-poly-L-lysines prepared by a synthesis in stages according to the process forming the subject matter of the invention have revealed that molecules having from 8 to 12 BPO groups on a corresponding group of 8 to 12 lysine radicals are optimally effective to provoke the immediate allergic reactions specific of the BPO.

Although smaller molecules such as $BPO_2Lys_2$ or $BPO_4Lys_4$ are also capable of provoking immediate reactions of the allergic type, it seems dangerous to use them, as such molecules may provoke, during cutaneous tests on a sensitive individual a generalised allergic reaction instead of a strictly localised reaction of the skin. Smaller molecules of BPO-poly-L-lysine than 6 units regularly provoke such generalised reactions in sensitized guinea pigs.

Consequently, studies made with the preparations of homogeneous BPO-poly-lysine of various molecular sizes according to the invention have, for the first time, made it possible to characterize the optimal size and configuration of the penicilloyl-poly-lysines (PPL) to be used in the skin tests for revealing allergy to penicillin.

Thus, it has been found that, to obtain reproducible results with the skin tests, but with no risk of provoking generalised reactions, it is firstly necessary to obtain a homogeneous L-lysine polymer support, i.e. of which all the molecules have the same degree of polymerisation and, on the other hand, these lysine polymers must comprise between 8 to 20 and preferably from 8 to 12 L-lysine linkages, so as to fix from 8 to 12 BPO groups to form the penicilloyl-poly-lysines according to the invention.

It has been shown that the preparations according to the invention are favourably compared with heterogeneous PPL preparations obtained from poly-lysine polymerised at random and having 20 lysine linkages (mean of the molecular weights) in the immediate skin reactions in patients sensitive to penicillin: these results are given in the following Table.

TABLE

Reactions of erythema and of papules to various PPL

| BPO derivative of the Compound | Homogeneous | | | | Heterogeneous | |
| --- | --- | --- | --- | --- | --- | --- |
| | $PPL_{5-5}$ E | $PPL_{20}$ D | $PPL_9$ A | $PPL_8$ B | $PPL_n$ | MDM |
| Patients having presented an allergy to penicillin | | | | | | |
| 15848/80 | +++ | ++ | + | + | ± | ± |
| 15864/80 | +++ | +++ | +++ | + | + | +++ |
| 15906/80 | ++ | ++ | (+) | (+) | − | − |
| 15927/80 | +++ | ++ | + | + | ++ | − |
| Patients never having presented an allergy to penicillin | | | | | | |

TABLE-continued
Reactions of erythema and of papules to various PPL

| BPO derivative of the Compound | Homogeneous | | | | Heterogeneous | |
|---|---|---|---|---|---|---|
| | PPL$_{5.5}$ E | PPL$_{20}$ D | PPL$_9$ A | PPL$_8$ B | PPL$_n$ | MDM |
| 20 patients | — | — | — | — | — | |

PPL$_n$: heterogeneous PPL (average 20 lysine radicals, such as those used in the skin tests of 1962 to 1980)
MDM: Minor determinant mixture (benzylpenicillin 1000 U/ml and sodium benzylpenicilloate 0.5 mg/ml).

It has also been shown that the compounds according to the invention have the advantage of being rapidly eliminated by the renal route and of not presenting immunogenicity (i.e. sensitization after repeated tests).

Since a crossed reactivity between various antibiotics of the β-lactam type with various side chains is based on the presence of antibodies directed against the β-lactam nucleus, the penicilloyl-polylysines prepared with benzylpenicillin also enable allergies to the other β-lactam antibiotics to be revealed. However, in some patients who have been sensitized by other antibiotics of the β-lactam type, a sensitivity exclusive to the corresponding side chain is produced. In such cases, preparations according to the invention obtained by combining homogeneous polylysines with β-lactam antibiotics other than benzylpenicillin will be used.

The present invention therefore relates firstly, as new products which may be used as support for the preparation of products of diagnosis, to L-lysine polymers of which all the molecules have the same degree of polymerisation and contain from 8 to 20 L-lysine linkages. The following polymers may be mentioned as examples of supports thus used:

A: H—Lys$_8$OH
B: Acetyl-Lys$_8$—OH
C: H—Lys$_{10}$—OH
D: H—Lys$_{20}$OH
E: CH$_2$—CO—Lys$_5$—OH
   |
   CH$_2$—CO—Lys$_5$—OH in which formulae the expression Lys represents a lysine radical of formula:

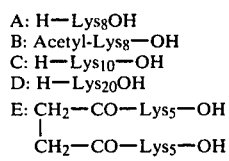

The process for preparing a lysine polymer according to the invention is characterised in that a two-phase method is used; starting from a derivative of lysine on the terminal carbon, an oligomer chain of lysine is formed step by step in a hydrophobic solvent by adding a suitably activated and protected lysine derivative to a protected chain of which the terminal α nitrogen is deblocked, at each cycle of elongation. Suitably activated and protected lysine derivatives which may be used are, for example, on the one hand, the tert-butylic ester of lysine of which the nitrogen in ε is protected by a tert-butyloxycarbonyl group, of formula:

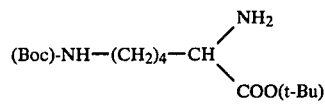

and, on the other hand, the lysine of which the nitrogen in α is protected by the p-nitrophenyl-sulfenyl group and the nitrogen in ε is protected by the tert-butyloxycarbonyl group of formula:

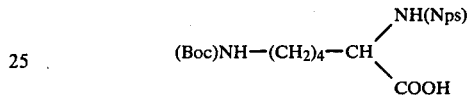

The purification of the intermediaries is effected by a liquid-liquid extraction. Using suitable solvents such as methylene chloride, methylene chloride mixed with dimethylformamide or dimethylformamide mixed with dimethylsulfoxide, lysine polymers are thus obtained, per stage, of the type: H—Lys$_n$—OH, formula in which n may go as far as 8 to 10, i.e. the octa- and deca-lysines. These lysine oligomers may be condensed in longer chains, after partial deprotection respectively of the terminal nitrogen and carbon, using as condensation agent carbodiimides in the presence of benzotriazole. Longer chains may also be obtained, of the type:

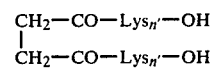

(in which formula n' is a whole number from 4 to 10) by condensing these suitably protected oligomers and after partial deprotection of the terminal nitrogen, with cross-linking molecules such as succinic acid, and other bifunctional molecules. The entirely protected polylysine molecules are totally deblocked by methods which depend on the protector groups, mostly by acidolysis and, in particular, by acidolysis by trifluoroacetic acid or by hydrochloric acid in the organic solvents when the protector group of nitrogen is the tert-butyloxycarbonyl group (Boc) and when the protector group of the carboxylic function is an ester of tert-butyl (OtBu).

The invention also relates, as products of diagnosis, to the penicilloyl derivatives of the lysine polymers according to the invention; the reaction of penicilloylation may be effected by incubation of the lysine polymers dissolved in alkali medium with a penicillin, a cephalosporin or, more generally, an antibiotic of β-lactam type. In this case, a stable bond is produced between the carboxylic group of penicilloic acid and the amino groups of the molecules of the support (Schneider & de Weck, Helv. Chim acta 49, 1695 (1966).

The following examples are intended to illustrate the process for preparing, on the one hand, the lysine polymers and, on the other hand, the products of conjugation with the penicillins, according to the invention.

In the following, the abbreviations used have the following meanings: Boc=tert-butyloxycarbonyl; Nps=p-nitrophenylsulfenyl; OtBu=tert-butylester; DCHA=dicyclohexylamine; EDCD=N-ethyl-N'-(3-dimethylaminopropyl)- carbodiimide. HCl; Et₃N=triethylamine; HOBt: 1-hydroxybenzotriazole; TFA=trifluoroacetic acid; THF=tetrahydrofuran; DMF=dimethylformamide. The characterisation of the products was made by thin layer chromatography (TLC) on plate of silica 60 F₂₅₄ sold by Merck Darmstadt and on paper (MN 214, Machery-Nagel, Düren) with quantities of 50 to 100 μg. The solvent system A is a mixture of chloroform and of methanol (9/1).

EXAMPLE 1

Synthesis of tert-butylic Lys(Boc)-Lys(Boc)-Lys(Boc)-Lys(Boc) Lys(Boc)-OtBu ester of penta-L-lysine of which all the amino groups are protected, except the terminal amino group.

Stage 1:

The Lys(Boc)-Otbu. acetate (2.0 g, or 5.5 millimoles) in 100 ml of methylene chloride is extracted with 0.3 M potassium carbonate in water, is dried over sodium sulfate and taken up dry in vacuo to obtain the residue I a. α-Nps-ε-Boc-Lys-OH.DCHA (3.2 g or 5.5 millimoles) in 200 ml of methylene chloride is extracted with 1.5 equivalent of a solution of acid sodium sulfate and with water, is dried over sodium sulfate and taken up dry in vacuo to obtain the residue I b.

The residues I a and I b are mixed with 1.2 g of EDCD (excess of 10%)+820 mg (or 5.5 millimoles) of HOBt and Et₃N up to pH>7 in 20 ml of THF; the mixture is left to react for 1 hour at 0° C., then 4 hours at ambient temperature. The reaction mixture is diluted with 400 ml of methylene chloride, it is extracted with 3 liters of 0.1 M hydrochloric acid, 1 liter of water, 3 liters of 0.3 M potassium carbonate and 2 liters of water. The solution is dried with sodium sulfate and evaporated in vacuo. Product I is obtained, viz. 3.74 g (99%) in the form of a yellow foam. TLC in solvent A: principal stain $R_f 0.71$ (yellow), stains in the form of traces: $R_f$ 0.78 and $R_f 0.60$ (UV).

Deprotection is then effected as follows: the product I (3.74 g) in 150 ml of methylene chloride+20 ml of methanol+20 ml of acetic acid+1.85 g of 1-(2-methylindolyl)-acetic acid +840 mg of ammonium thiocyanate are stirred for 40 mins. in the dark; the mixture is diluted with 400 ml of CH₂Cl₂, extracted with 4 liters of 0.3 M potassium carbonate, 2 liters of water and dried over sodium sulfate. Evaporation in vacuo leaves a product I (deprotected): 2.75 g (or 5.2 millimoles) in the form of yellow foam. TLC in solvent A, principal stain, $R_f 0.18$ (fluram, ninhydrin), a stain in the form of trace $R_f 0.76$ (UV).

Stage II:

2.75 g of product I (deprotected) and 5.3 millimoles of α-Nps-ε-Boc-Lys-OH+1.1 g of EDCD+800 mg of HOBt+Et₃N are mixed up to pH>7 in 20 ml of THF, the mixture is left to react for 1 hour at 0° C., then 20 hours at ambient temperature. The reaction mixture is diluted with methylene chloride, extracted with 3 liters of 0.1 M HCl, 1 liter of water, 3 liters of 0.3 M potassium carbonate and 2 liters of water. The solution is dried over sodium sulfate and evaporated in vacuo. Product II is obtained: 4.66 g (5.1 millimoles) yellow foam. TLC in solvent A: principal stain $R_f 0.58$ (yellow), trace at $R_f$ 0.77 (UV).

Deprotection of the product II is effected in the following manner: 4.66 g of product II in 150 ml of methylene chloride+20 ml of methanol+20 ml of acetic acid+1.85 g of 1-(2-methylindolyl)-acetic acid+780 mg of ammonium thiocyanide are mixed and stirred in the dark for 40 mins.; the mixture is diluted with methylene chloride up to 300 ml, extracted with 4 liters of 0.3 M potassium carbonate, 2 liters of water and dried over sodium sulfate. Evaporation in vacuo leaves a product II (deprotected): 3.63 g (or 4.8 millimoles) yellow foam. TLC in the solvent A: principal stain, $R_f 0.18$ (fluram, ninhydrin), trace of $R_f 0.79$ (UV).

Stage III:

3.63 g of product II (deprotected) and 5.0 millimoles of α-Nps-ε-Boc-Lys-OH+1.1 g of EDCD+750 mg of HOBt+Et₃N at pH>7 in 20 ml of THF are mixed. The mixture is left to react for 1 hour at 0° C. and 65 hours at ambient temperature. The reaction mixture is then treated as in stage II and product III is obtained: 5.6 g (4.9 millimoles) yellow foam. TLC in solvent A: principal stain, $R_f 0.54$ (yellow), trace at $R_f 0.77$ (UV). Deprotection: 5.6 g of product III are added in 150 ml of methylene chloride+20 ml of methanol+20 ml of acetic acid+1.80 g of 1-(2-methylindolyl)-acetic acid+760 mg of am monium thiocyanide and the mixture is stirred in the dark for 40 mins; it is diluted with methylene chloride up to 300 ml, extracted with 4 liters of 0.3 M potassium carbonate, 2 liters of water and dried over sodium sulfate. Evaporation in vacuo yields a product III (deprotected): 4.66 g (or 4.7 millimoles) yellow foam. TLC in solvent A: principal stain, $R_f 0.18$ (fluram, ninhydrin), trace at $R_f 0.78$ (UV). Stage IV:

4.66 g of product III (deprotected), 4.8 millimoles of α-Nps-ε-Boc-Lys-OH+1.05 g of EDCD+720 mg of HOBt+Et₂N at pH>7 in 20 ml of THF+2 ml of DMF are mixed; the mixture is left to react for 1 hour at 0° C., then 18 hours at ambient temperature. The reaction mixture is treated as in stage II and product IV is obtained: 6.4 g (4.7 millimoles) yellow foam. TLC in A: principal stain, $R_f 0.51$ (yellow), trace of $R_f 0.77$ (UV). Deprotection of the product IV is effected by adding 4.9 g of product IV (3.6 millimoles) in 100 ml of methylene chloride+15 ml of methanol+15 ml of acetic acid+1.33 g of 1-(2-methylindolyl)-acetic acid+530 mg of ammonium thiocyanide and the mixture is stirred in the dark for 45 mins., diluted with methylene chloride up to 200 ml and extracted with 2.5 liters of 0.3 M potassium carbonate, 1.5 liter of water and dried over sodium sulfate. Evaporation in vacuo yields a deprotected product: 4.1 g (3.4 millimoles) yellowish foam. TLC in A: principal stain $R_f 0.18$ (fluram, ninhydrin), trace at $R_f 0.78$ (UV).

EXAMPLE 2

Process for preparation of

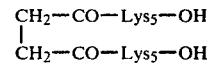

2.0 g, or 1.65 millimoles, of product IV (deprotected), or: H-[Lys(Boc)]₅-OtBu in 10 ml of THF/DMF (3:2) are reacted with 200 mg (2 millimoles) of succinic anhydride by adding Et₃N to maintain the pH at approximately 8. After 2 hours, 0.1 ml of diethylaminoethylamine is added and the mixture is stirred continuously for a further hour. After dilution up to 300 ml with methylene chloride, the reaction solution is extracted with 0.6 liter of 0.1 M HCl, 0.4 liter of water, it is dried over sodium sulfate and evaporated in vacuo and 2.1 g of a yellowish residue of succinylated pentapeptide are obtained. TLC in solvent A: a stain of $R_f0.12$, in dioxan/water (5:1), a stain $R_f 0.80$ (in 2,6-dichlorophenol-indophenol, ninhydrin after heating).

This product in 10 ml of DMF is neutralised by Et$_3$N and mixed with 350 mg of EDCD (10% excess) added in three portions for 1 hour. After a further hour, the sludge is concentrated to half its volume in vacuo at 30° C. and the temperature is maintained at ambient temperature for 72 hours. After dilution with 20 ml of DMF, the clear solution is added drop by drop to 500 ml of water with stirring. The precipitate is collected by filtration, resuspended in water for 30 mins. and filtered again. After drying with water-jet pump, 3.60 g (1.43 millimole) of an amorphous, slightly yellowish powder are obtained. TLC in solvent A: principal stain $R_f 0.40$ (Hoppe-Reindel reagent; ninhydrin after prolonged heating), trace $R_f 0.18$ (fluram), $R_f 0.0$ (Hoppe-Reindel reagent).

The protected succinyldipentalysine (3.60 g) is maintained in 30 ml of TFA for 1 hr. at ambient temperature, then evaporated in vacuo and the oily residue suspended in ether. The solidified mass is separated from the solvent by decantation, washed three times in ether, filtered and dried in vacuo; 4.2 g of a whitish powder are obtained. Electrophoresis on thin layer of cellulose F (Merck) gives a principal zone, 72 mm towards the cathode, a trace, 81 mm (ninhydrin), pyridine/acetic acid/water (1/9/90) pH 3.6, 36 volts/cm, 20 mins. The deprotected trifluoroacetate of succinyl-dipentaylsine obtained (3.75 g, 14 millimoles of NH$_2$ groups) in 20 ml of water is mixed with 10 ml of 2 N hydrochloric acid and the solution is evaporated in vacuo. This evaporation is repeated twice after addition of water. The residue is taken up in 30 ml of water, neutralised with 1 N sodium hydroxide and maintained for 30 mins. with charcoal after dilution up to 200 ml by water. The suspension is filtered on Celite and the filtrate is passed, after concentration up to 5 ml, through a Sephadex-G-25 M column of 2.5×10 cm at the speed of 30 ml/hr. by means of water, in order to eliminate the greater part of the salts. The peak characterising the oligolysine was revealed by Folin colorimetric analysis. The corresponding fractions were collected, concentrated up to 5 ml and the concentrate passed through a Sephadex G-25 M column of 2.5×48 cm, at the speed of 50 ml/hr. by means of water. The eluted product revealed by Folin colorimetry was recovered by lyophilisation to yield 2.7 g of a foamy, whitish, very hygroscopic product.

Electrophoresis: on paper (MN 214, Machery-Nagel): single zone, 52 mm towards the cathode, 20 mins.; on cellulose F in thin layer: single zone, 72 mm towards the cathode, 20 mins.; on thin layer silica gel (FG 60 F$_{254}$, Merck), single zone, 10 mm towards the cathode, 30 mins. Pyridine/acetic acid/water (1/9/90) pH 3.6, 36 volts/cm. Detection with ninhydrin.

EXAMPLE 3

Preparation of

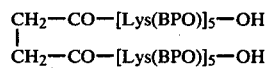

120 ml of decahydrochloride of

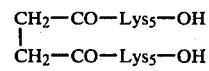

in 1 ml of water are taken to pH 10 with 2 M potassium carbonate, then 260 mg of the potassium salt of benzylpenicillin as well as 5 N sodium hydroxide are added to maintain the pH above 11. After two hours at ambient temperature, an additional portion of 260 mg of penicillin is added. After 24 hours at pH 11, the pH is lowered to 8 with 1 N hydrochloric acid and the solution is diluted to 4 ml with water. This solution is chromatographed on an Sephadex-G-25 column of 2.5×28 cm at the speed of 22 ml/hr. with 0.01 M PBS at pH 7.4. The fractions presenting stable penamaldate values (Schneider & de Weck, Helv. Chim. Acta 49, 1689 (1966) are joined and evaporated in vacuo at 30° C. to obtain a whitish residue which is dissolved in 4 ml of water and passes through a Sephadex-G-10 column of 1.9×30 cm at the speed of 20 ml/hr. with water. The fractions presenting stable penamaldate values are joined and lysophilised: 300 mg of a white product are obtained (loss of weight by drying in vacuo over potassium hydroxide at 45° C.: 3%). TLC in the butanol/acetic acid/water (4/1/1): a stain $R_f 0.58$; in ethyl acetate/acetic acid/water (3/1/1): a stain $R_f 0.76$; in dioxan/water (3/1): a stain $R_f 0.61$ (Hoppe-Reindel reagent; iodazide). Electrophoresis on paper under high voltage: single zone 69 mm towards the anode (Hoppe-Reindel reagent; iodazide; negative with fluram) 36 volts/cm, 30 mins. Value of penamaldate (PV$_{molar}$): 176000 l.mol$^{-1}$.cm$^{-1}$; penamaldate stability (PS$_{10}$): 95%. An aliquot part is converted into free acid by precipitation of an aqueous solution with the acid potassium sulfate. The precipitate is centrifuged, washed with water and dried in vacuo over P$_2$O$_5$: C$_{224}$H$_{306}$N$_{40}$O$_{54}$S$_{10}$(4743.9)

Calculated: N 11.81, S 6.76%,
Found (corrected for 1.66% ash): N 11.53, S 6.50%.

What is claimed is:

1. A lysine polymer of the formula:

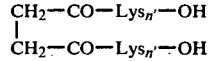

where each n' is the same whole number, said number being between 4 and 10, and Lys has the formula:

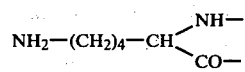

2. The Lysine polymer of claim 1, wherein n' is the whole number 5.

* * * * *